US010413218B2

(12) United States Patent
Yamato et al.

(10) Patent No.: US 10,413,218 B2
(45) Date of Patent: Sep. 17, 2019

(54) WRISTBAND-TYPE ARM MOVEMENT DETERMINATION DEVICE AND WRISTBAND-TYPE ACTIVITY TRACKER

(71) Applicant: TDK Corporation, Minato-Ku, Tokyo (JP)

(72) Inventors: Kumiko Yamato, Kawasaki Kanagawa (JP); Kazunori Hashimoto, Konosu Saitama (JP)

(73) Assignee: TDK Corporation, Tokyo (JP)

( * ) Notice: Subject to any disclaimer, the term of this patent is extended or adjusted under 35 U.S.C. 154(b) by 575 days.

(21) Appl. No.: 14/483,992

(22) Filed: Sep. 11, 2014

(65) Prior Publication Data

US 2015/0198460 A1 Jul. 16, 2015

(30) Foreign Application Priority Data

Jan. 15, 2014 (JP) ................................. 2014-005352

(51) Int. Cl.
*G01C 22/00* (2006.01)
*A61B 5/11* (2006.01)
*A61B 5/00* (2006.01)

(52) U.S. Cl.
CPC ........... *A61B 5/1118* (2013.01); *A61B 5/1123* (2013.01); *A61B 5/681* (2013.01);
(Continued)

(58) Field of Classification Search
None
See application file for complete search history.

(56) References Cited

U.S. PATENT DOCUMENTS 6,241,684 B1 * 6/2001 Amano .............. A61B 5/02438
600/503
6,369,794 B1 * 4/2002 Sakurai ................... G06F 3/017
345/156
(Continued)

FOREIGN PATENT DOCUMENTS

JP 2002-298245 A 10/2002
JP 2005-352739 A 12/2005
(Continued)

OTHER PUBLICATIONS

Japanese Office Action dated May 23, 2017 issued in corresponding Japanese Patent Application No. 2014-005352.
(Continued)

*Primary Examiner* — Janet L Suglo
*Assistant Examiner* — Leonard S Liang

(57) ABSTRACT

According to an embodiment, an activity tracker includes an acceleration sensor capable of detecting accelerations in directions of two or more axes orthogonal to each other, an arm motion determination unit configured to determine on the basis of an output from the acceleration sensor whether there is a predetermined motion within a predetermined time period, when operation of an operation button is detected, and a transmission processing unit configured to cause a lamp to glow and wirelessly transmit a piece of corresponding information corresponding to the predetermined motion and a piece of time information at a time of detecting that there is the predetermined motion, when it is determined by the arm motion determination unit that there is the predetermined motion.

6 Claims, 12 Drawing Sheets

(52) U.S. Cl.
CPC ............. *A61B 5/6824* (2013.01); *A61B 5/112* (2013.01); *A61B 2562/0219* (2013.01)

(56) References Cited

U.S. PATENT DOCUMENTS

| | | | |
|---|---|---|---|
| 6,571,193 | B1 | 5/2003 | Unuma et al. |
| 6,941,239 | B2 | 9/2005 | Unuma et al. |
| 7,212,943 | B2 * | 5/2007 | Aoshima ............... G01C 22/006 702/141 |
| 8,744,804 | B2 * | 6/2014 | Messenger ............. G06Q 30/02 702/160 |
| 8,751,194 | B2 * | 6/2014 | Panther ............... G06F 3/04883 702/160 |
| 9,110,505 | B2 * | 8/2015 | Mastandrea, Jr. ....... G06F 3/014 |
| 2003/0176815 | A1 * | 9/2003 | Baba .................. A61B 5/02438 600/595 |
| 2004/0116837 | A1 * | 6/2004 | Yamaguchi ........ A61B 5/02438 600/595 |
| 2004/0186695 | A1 * | 9/2004 | Aoshima .............. G01C 22/006 702/190 |
| 2006/0161079 | A1 * | 7/2006 | Choi ..................... A61B 5/1117 600/595 |
| 2006/0195020 | A1 * | 8/2006 | Martin ................ G06F 19/3475 600/301 |
| 2006/0220882 | A1 * | 10/2006 | Makino ............... A63B 69/0028 340/573.1 |
| 2006/0235642 | A1 * | 10/2006 | Vock .................... A42B 3/0433 702/141 |
| 2008/0171915 | A1 * | 7/2008 | Kawajiri ............ A61B 5/02241 600/300 |
| 2009/0143199 | A1 * | 6/2009 | Nishibayashi ........ A61B 5/1118 482/8 |
| 2009/0164219 | A1 * | 6/2009 | Yeung .................... G04C 3/002 704/258 |
| 2010/0100012 | A1 * | 4/2010 | Matsumura ........... A61B 5/1118 600/595 |
| 2012/0274554 | A1 * | 11/2012 | Kinoshita ............. A61B 5/1118 345/156 |
| 2013/0138394 | A1 * | 5/2013 | Shiga ................... G01C 22/006 702/160 |
| 2013/0158686 | A1 * | 6/2013 | Zhang ................. G01C 22/006 700/91 |
| 2013/0332286 | A1 * | 12/2013 | Medelius ................ A61B 5/01 705/14.66 |
| 2014/0074431 | A1 * | 3/2014 | Modi ................... G01C 22/006 702/160 |

FOREIGN PATENT DOCUMENTS

| | | |
|---|---|---|
| JP | 2006-101973 A | 4/2006 |
| JP | 2006-110180 A | 4/2006 |
| JP | 2006-285642 A | 10/2006 |
| JP | 4379214 B2 | 12/2009 |
| JP | 2010-041302 A | 2/2010 |
| JP | 2010-146223 A | 7/2010 |
| JP | 2011-103087 A | 5/2011 |
| JP | 4705358 B2 | 6/2011 |
| JP | 2012-237719 A | 12/2012 |
| WO | 2010-146811 A1 | 12/2010 |
| WO | 2013-024461 A1 | 2/2013 |

OTHER PUBLICATIONS

Japanese Office Action dated Mar. 6, 2018 issued in corresponding Japanese Patent Application No. 2013-249690.

* cited by examiner

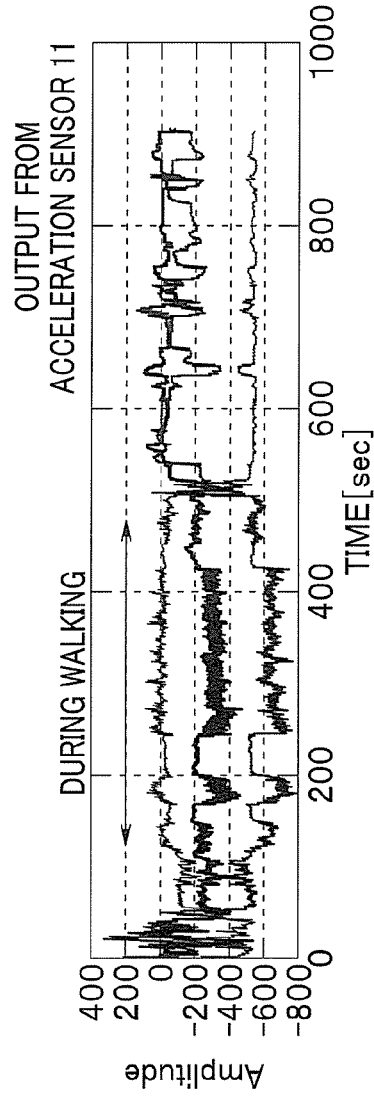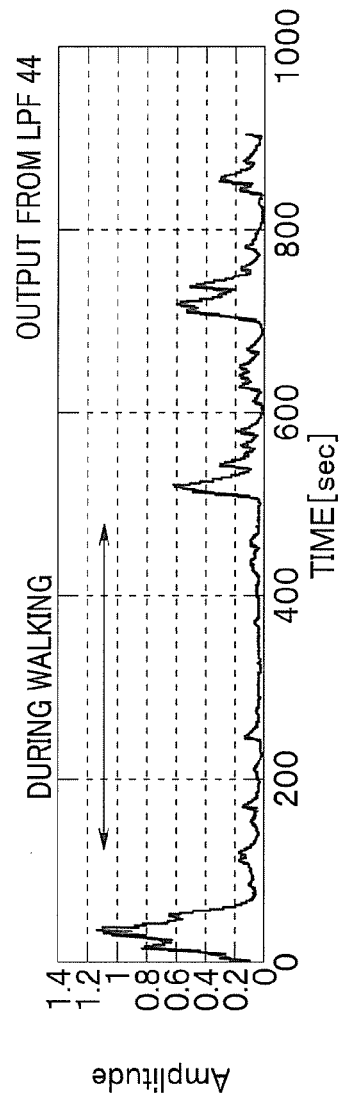

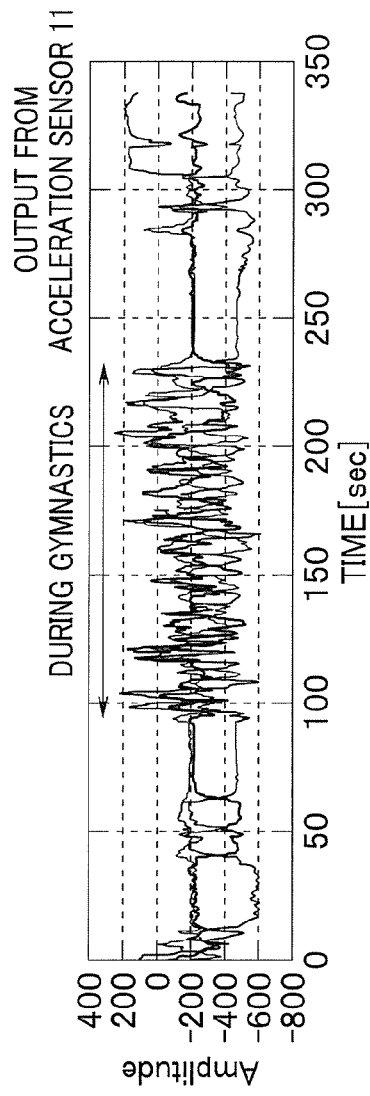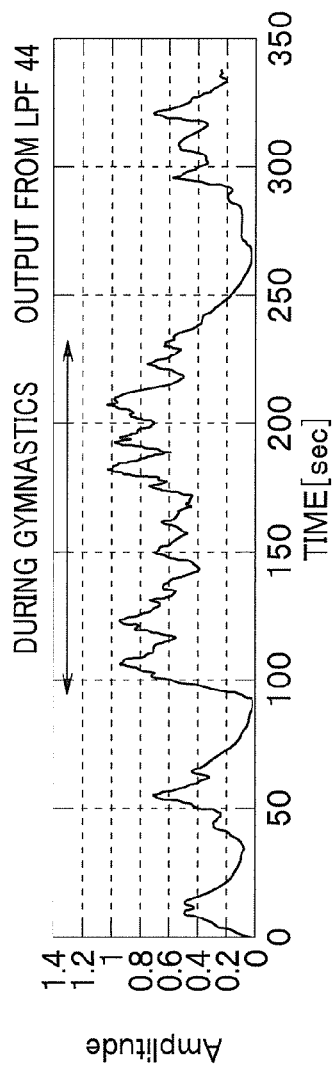

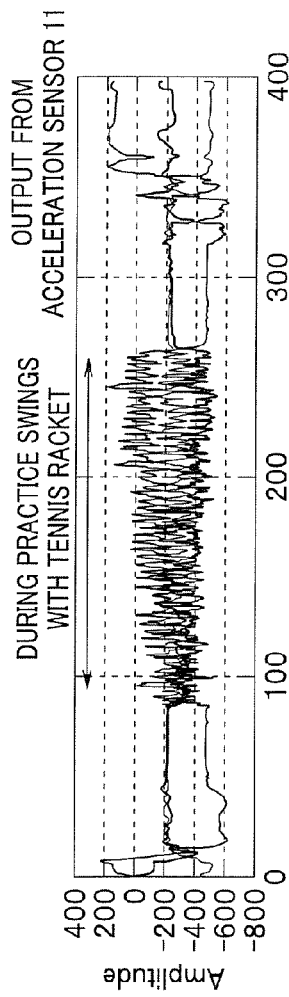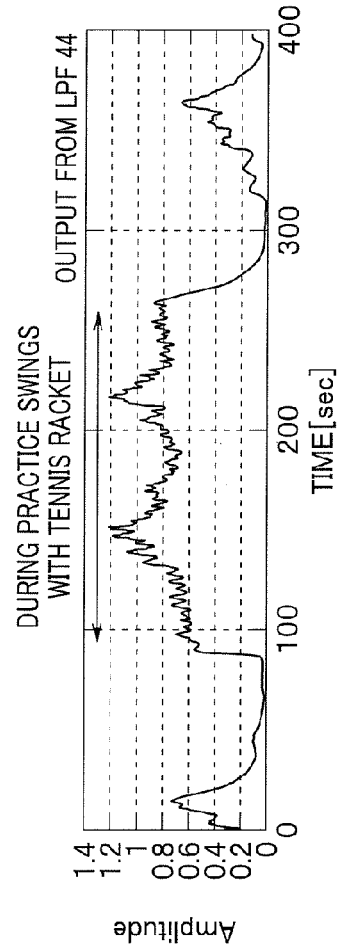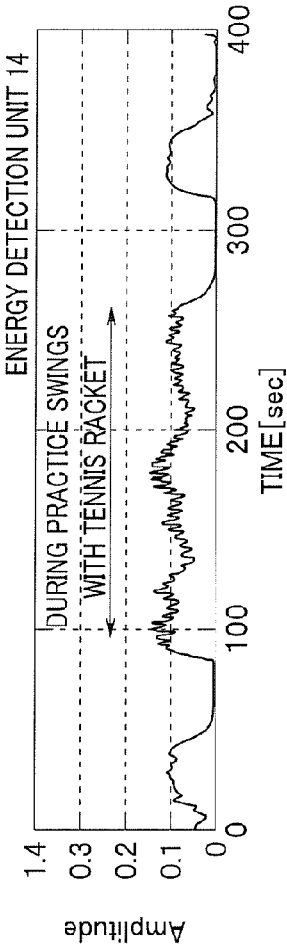

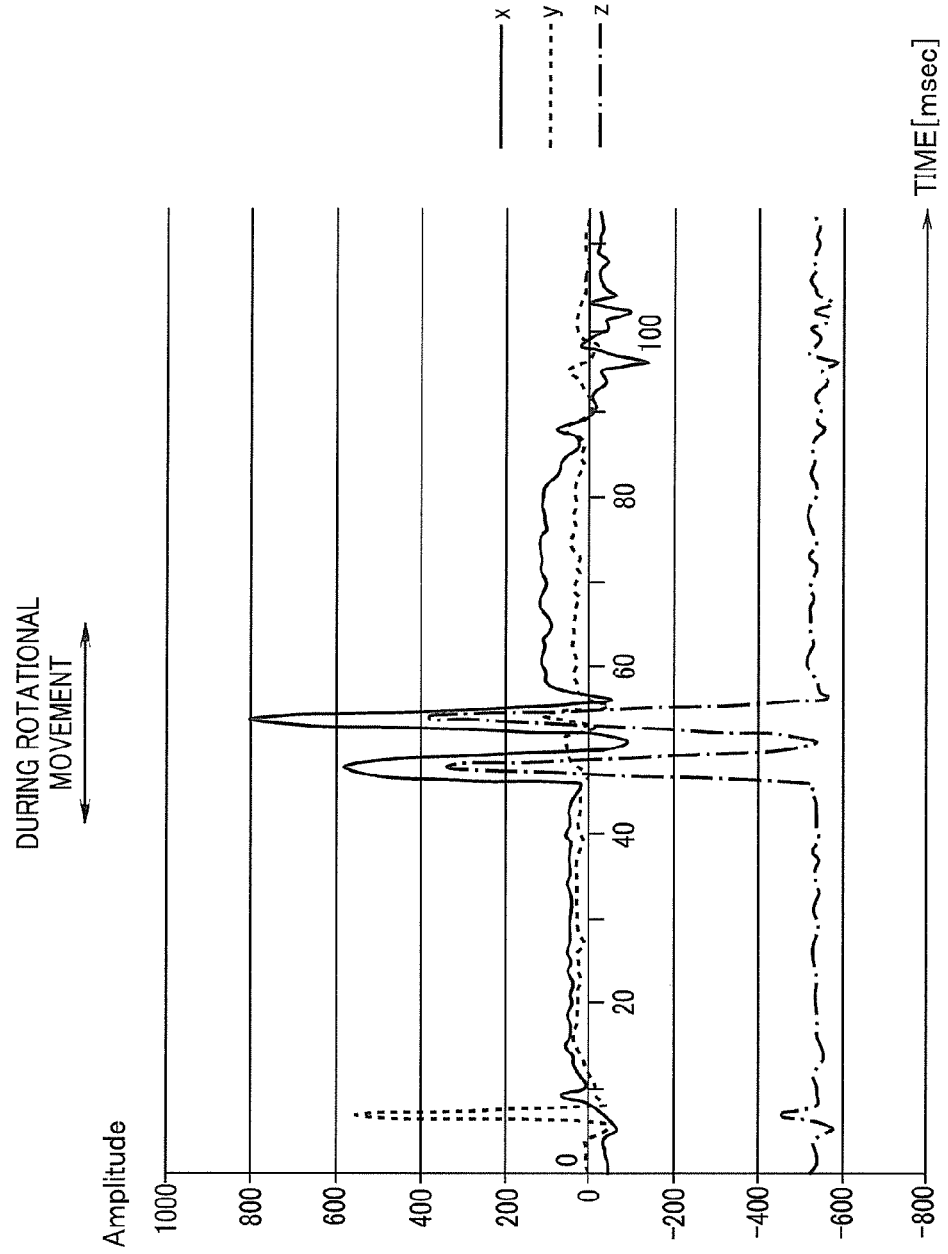

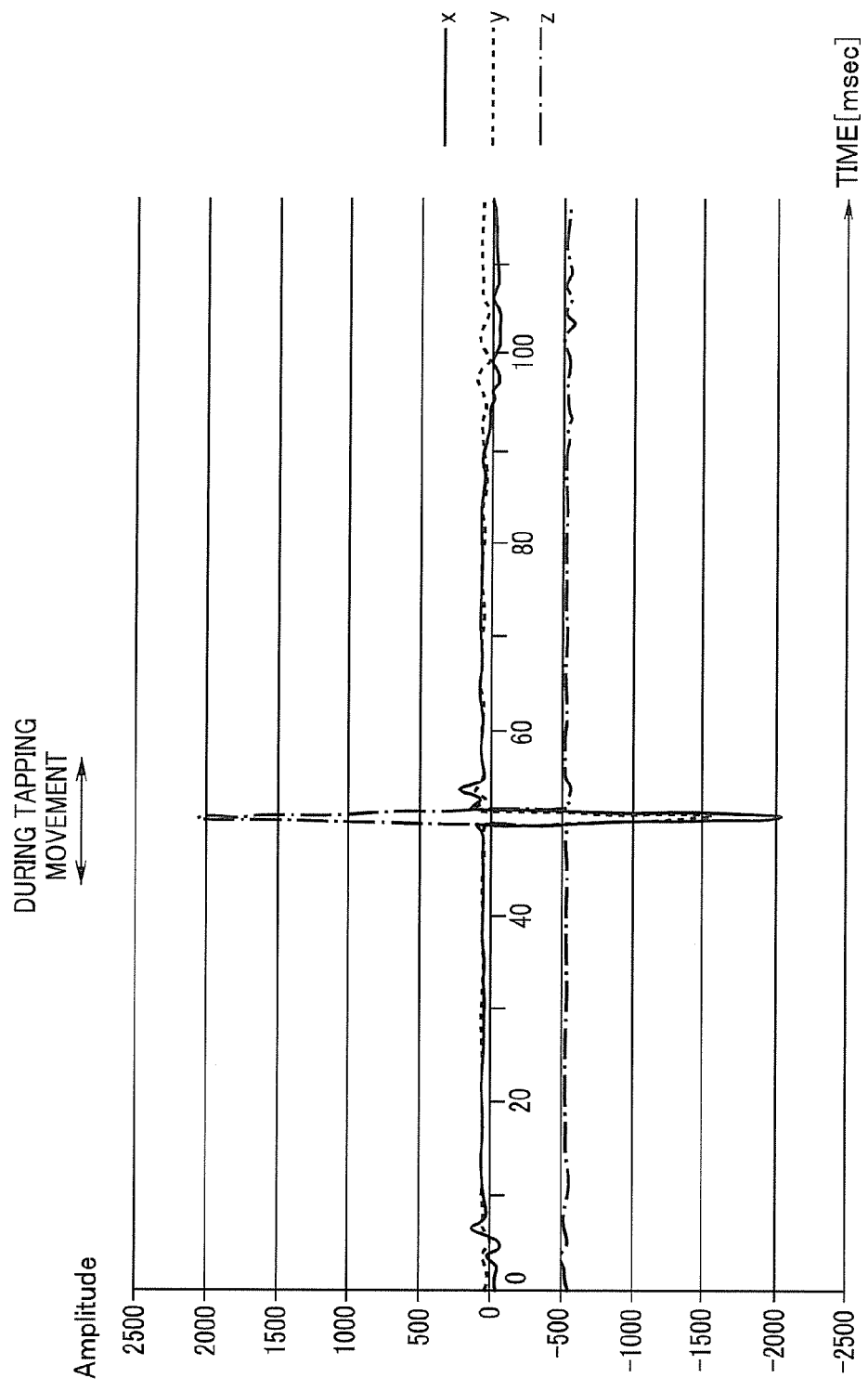

| EVENT CODE | TIME |
|---|---|
| . . . | . . . |
| 1 | 2013. 12. 19. 07. 30 |
| 2 | 2013. 12. 19. 08. 10 |
| 1 | 2013. 12. 19. 12. 35 |
| 2 | 2013. 12. 19. 13. 00 |
| . . . | . . . |

TBL

WRISTBAND-TYPE ARM MOVEMENT DETERMINATION DEVICE AND WRISTBAND-TYPE ACTIVITY TRACKER

CROSS-REFERENCE TO RELATED APPLICATION

This application is based upon and claims the benefit of priority from the Japanese Patent Application No. 2014-005352 filed on Jan. 15, 2014; the entire contents of which are incorporated herein by reference.

FIELD

An embodiment described herein relates generally to a wristband-type arm movement determination device and a wristband-type activity tracker.

BACKGROUND

Pedometers which count a number of steps of a person have been in widespread use. Activity trackers which measure an amount of activity of a person are sold these days. In recent years, instruments have been proposed which record living body data, such as electrocardiogram data, an action of a person, and the like.

Some of the instruments are worn on, for example, an arm or a belt of a person to detect a motion of the person with an acceleration sensor and determine presence or absence of a predetermined motion of the person on the basis of an output value from the acceleration sensor.

Conventional pedometers and the like and the proposed instruments, however, constantly monitor an output from an acceleration sensor and perform determination processing as to whether there is a predetermined motion. There is a not-so-small possibility that an unintended motion of a user may be wrongly determined to be a predetermined motion.

Additionally, the determination processing as to whether there is a predetermined motion is performed on the basis of the output from the acceleration sensor, which increases power consumption of an instrument using an electronic circuit, such as a central processing unit (CPU).

BRIEF DESCRIPTION OF THE DRAWINGS

FIGS. 7A and 7B are graphs for explaining examples of outputs from the acceleration sensor 11 and the gravity detection unit 15 during walking, according to the present embodiment;

FIGS. 8A and 8B are graphs for explaining examples of outputs from the acceleration sensor 11 and the gravity detection unit 15 during gymnastics, according to the present embodiment;

FIGS. 10A, 10B, and 10C are graphs for explaining examples of outputs from the acceleration sensor 11, the gravity detection unit 15, and the acceleration energy detection unit 14 during practice swings with a tennis racket, according to the present embodiment;

FIG. 11 is a graph for explaining an example of individual outputs from the acceleration sensor 11 when there is a predetermined motion of an arm L, according to the present embodiment;

FIG. 12 is a graph for explaining another example of individual outputs from the acceleration sensor 11 when there is a predetermined motion of the arm L, according to the present embodiment;

DETAILED DESCRIPTION

A wristband-type arm movement determination device according to an embodiment is provided which includes an acceleration sensor capable of detecting accelerations in directions of two or more axes orthogonal to each other, a detection processing circuit configured to detect presence or absence of a predetermined signal which is not an output signal from the acceleration sensor, a determination circuit configured to determine on the basis of an output from the acceleration sensor whether there is a predetermined motion within a predetermined time period, when it is detected by the detection processing circuit that there is the predetermined signal, and a transmission processing circuit configured to wirelessly transmit a piece of corresponding information corresponding to the predetermined motion and a piece of time information at a time of detecting that there is the predetermined motion, when it is determined by the determination circuit that there is the predetermined motion.

The embodiment will be described below with reference to the drawings.

(Configuration)

Figure 1:
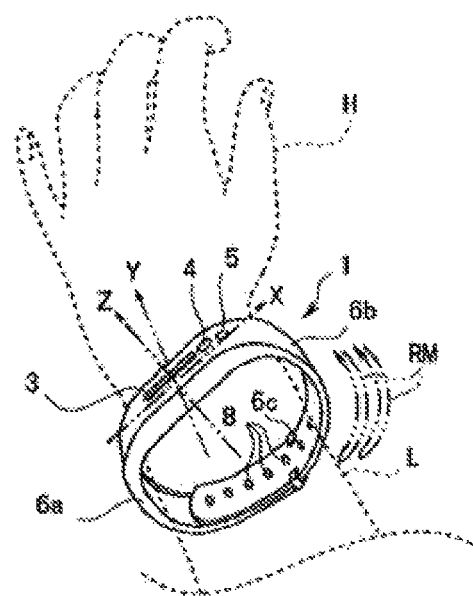
FIG. 1 is an external view of a wristband-type activity tracker according to the present embodiment.
Figure 2:
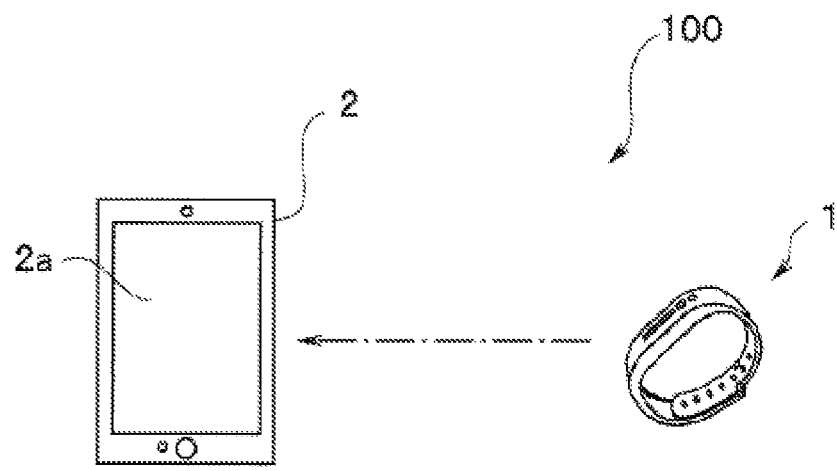
FIG. 2 is a configuration view of an action recording system composed of the wristband-type activity tracker and a smartphone, according to the present embodiment.

FIG. 1 is an external view of a wristband-type activity tracker 1 according to the present embodiment. FIG. 2 is a configuration view of an action recording system 100 which is composed of the wristband-type activity tracker and a smartphone.

The wristband-type activity tracker (hereinafter referred to as an activity tracker) 1 is an instrument capable of recording a piece of action information of a user and transmitting the piece of action information to a smartphone 2.

The activity tracker 1 has a belt-like wristband shape so as to be wrapped around and worn on an arm (indicated by dotted lines) L of a user and has an elongated operation button 3 provided at a central unit. A lamp 4 composed of a light-emitting diode (hereinafter referred to as an LED) is disposed adjacent to the operation button 3. A speaker 5 is also disposed adjacent to the lamp 4.

The operation button 3 is operated before or after the user performs a predetermined action, such as eating or medicine taking, as will be described later. The operation button 3 has a switch 3a (see FIG. 3) therein. As will be described later, when the operation button 3 is pressed, the switch 3a is turned on. It is determined whether a movement of the arm between the turn-on and after a lapse of a predetermined time period is a predetermined motion. Thus, the operation button 3 is an input device for the user to enter an arm movement determination instruction and is an operation unit configured to output a predetermined signal when the operation unit is operated.

The lamp 4 having the LED that is a light-emitting element is a notification unit configured to light up to inform the user when the above-described movement of the arm is determined to be the predetermined motion.

The speaker 5 is a sound output unit for outputting a predetermined sound or voice.

The activity tracker 1 has two bands 6a and 6b which extend from opposite sides of the central unit where the operation button 3 and the like are disposed. A fastener 6c is provided at an end unit of the band 6a, and a plurality of holes 8, into which a protruding unit (not shown) of the fastener 6c is to fit, are formed at predetermined intervals in the band 6b. The user can wear the activity tracker 1 on the arm L by fitting the protruding unit (not shown) formed at the fastener 6c into the hole 8 at an arbitrary position.

Note that although the two bands 6a and 6b and the central unit provided with the operation button 3 and the like in the activity tracker 1 according to the present embodiment are integrally molded from, e.g., a rubber member, the activity tracker 1 may be composed of a main body unit provided with the operation button 3 and the like and two bands connected to opposite sides of the main body unit, i.e., may be configured to have a main body unit and a band unit which are separate.

The operation button 3, the lamp 4, and the speaker 5 are arranged at the activity tracker 1 such that the operation button 3, the lamp 4, and the speaker 5 are disposed on an outside surface opposite to an inside surface of the activity tracker, which is in close contact with the arm L, of the activity tracker 1 when the activity tracker 1 is worn on the arm L of the user.

The action recording system 100 shown in FIG. 2 is an action recording system utilizing the activity tracker 1.

As will be described later, the activity tracker 1 has a wireless communication function and can transmit a piece of number-of-steps information, an estimated piece of action information, and a piece of event information to the smartphone 2. The user can transmit data, such as a piece of number-of-steps information, from the activity tracker 1 to the smartphone 2 and cause the data to be stored in a memory of the smartphone 2. The user can manage the data with an application program of the smartphone 2 and display the data on a display unit 2a of the smartphone 2.

Figure 3:
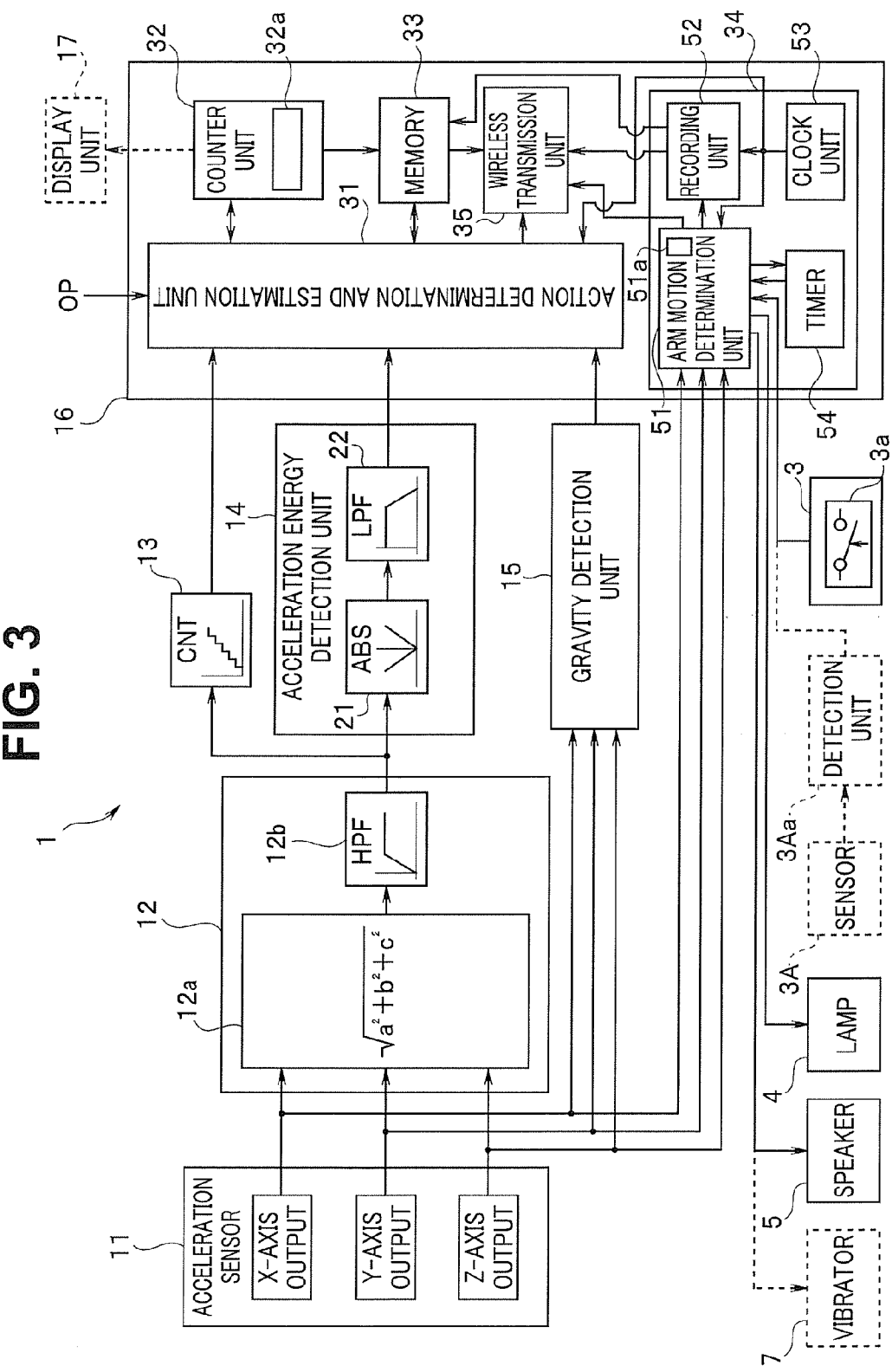
FIG. 3 is a block diagram showing a configuration of an activity tracker 1 according to the present embodiment.

FIG. 3 is a block diagram showing a configuration of the activity tracker 1 according to the present embodiment.

The activity tracker 1 is configured to include the operation button 3, the lamp 4, the speaker 5, an acceleration sensor 11, an acceleration detection unit 12, a step counter 13, an acceleration energy detection unit 14, a gravity detection unit 15, and a control unit 16. For example, components other than the operation button 3, the lamp 4, the speaker 5, and the acceleration sensor 11, or more specifically, the acceleration detection unit 12, the step counter 13, the acceleration energy detection unit 14, the gravity detection unit 15, and the control unit 16 are formed within a one-chip semiconductor device as a semiconductor integrated circuit.

The activity tracker 1 has a pedometer function, an amount-of-activity measurement function, and an event time recording and transmission function (to be described later).

Note that an on-off button for turning on or off power to the activity tracker 1, a reset button for resetting a count value, and the like are not shown in FIG. 1 and that an operation signal OP from the buttons are input to the control unit 16.

The acceleration sensor 11 has three sensors so as to be capable of detecting respective accelerations in directions of three axes (an X-axis, a Y-axis, and a Z-axis) orthogonal to one another and is a three-axis acceleration sensor configured to output an X-axis output, a Y-axis output, and a Z-axis output as acceleration signals for the respective axes. The individual outputs from the acceleration sensor 11 are input to the acceleration detection unit 12, the gravity detection unit 15, and an arm motion determination unit 51 to be described later.

As shown in FIG. 1, the user can wear the activity tracker 1 on the arm L such that the X-axis direction is a direction parallel to a plane of a back of a hand H and orthogonal to an axis of the arm L, the Y-axis direction is a direction parallel to the plane of the back of the hand H and parallel to the axis of the arm L, and the Z-axis direction is a direction orthogonal to the plane of the back of the hand H when the activity tracker 1 is worn on the arm L of the user. In FIG. 1, the arm L is passed through the bands 6a and 6b in the shape of a circular ring of the activity tracker 1 from a near side of the sheet surface toward the other side.

The acceleration detection unit 12 includes a root-sum-square calculation unit 12a and a high-pass filter (HPF) 12b.

The root-sum-square calculation unit 12a is a circuit configured to produce a signal as a root sum square of individual outputs from the acceleration sensor 11. Since accelerations in a plurality of directions (three directions, here) are used here, the root-sum-square calculation unit 12a configured to produce a signal as a root sum square of individual outputs is used. A sum-of-squares calculation circuit configured to produce a signal as a sum of squares may be used instead of the root-sum-square calculation unit 12a.

The high-pass filter 12b is an offset canceller circuit for removing a gravitational acceleration from an output from the root-sum-square calculation unit 12a.

Note that although the acceleration sensor 11 is a three-axis acceleration sensor here, the acceleration sensor 11 may be an acceleration sensor with two or more axes as long as the acceleration sensor detects accelerations in two or more directions.

Thus, the acceleration detection unit 12 detects an acceleration from outputs from the acceleration sensor 11 capable of detecting accelerations in directions of two or more axes orthogonal to each other and outputs an acceleration signal. The acceleration signal output from the acceleration detection unit 12 is input to the step counter (CNT) 13 and the acceleration energy detection unit 14.

The step counter 13 is a counter configured to count the number of steps on the basis of the acceleration signal output from the acceleration detection unit 12. The step counter 13 is a counter configured to increment by 1 when a value not less than a predetermined threshold is input. The step counter 13 counts the number of steps based on the acceleration signal during a predetermined time period (e.g., 5 seconds) and holds a count value.

The acceleration energy detection unit 14 includes an absolute value circuit 21 and a low-pass filter 22.

The acceleration signal input to the acceleration energy detection unit 14 is input to the absolute value circuit 21. The absolute value circuit 21 calculates an absolute value of the input acceleration signal and outputs the absolute value to the low-pass filter 22.

The low-pass filter 22 averages outputs from the absolute value circuit 21 to detect an acceleration intensity and outputs the acceleration intensity to an action determination and estimation unit 31 of the control unit 16. As described above, the acceleration energy detection unit 14 constitutes an acceleration intensity detection circuit configured to detect an acceleration intensity from an acceleration signal from the acceleration detection unit 12.

The gravity detection unit 15 detects changes in the individual axis directions with respect to a gravity direction and outputs a detection result (a determination signal to be described later) to the action determination and estimation unit 31.

Figure 4:
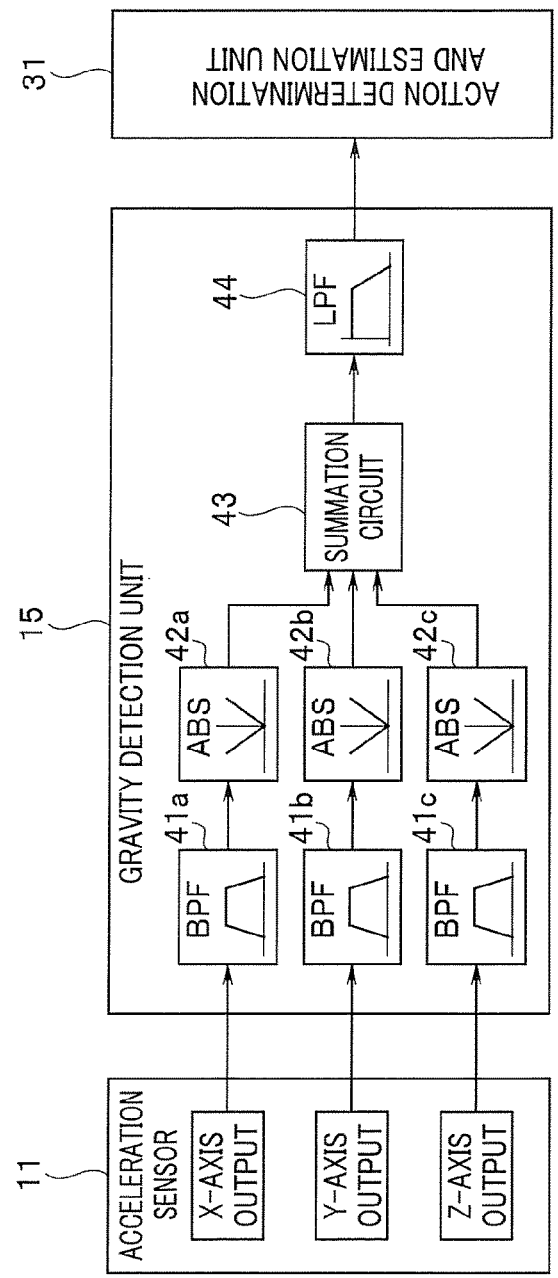
FIG. 4 is a block diagram for explaining a detailed circuit configuration of a gravity detection unit 15, according to the present embodiment.

FIG. 4 is a block diagram for explaining a detailed circuit configuration of the gravity detection unit 15. As shown in FIG. 4, the gravity detection unit 15 is configured to include three band-pass filters 41a, 41b, and 41c, three absolute value circuits 42a, 42b, and 42c, a summation circuit 43, and a low-pass filter 44.

Figure 5:
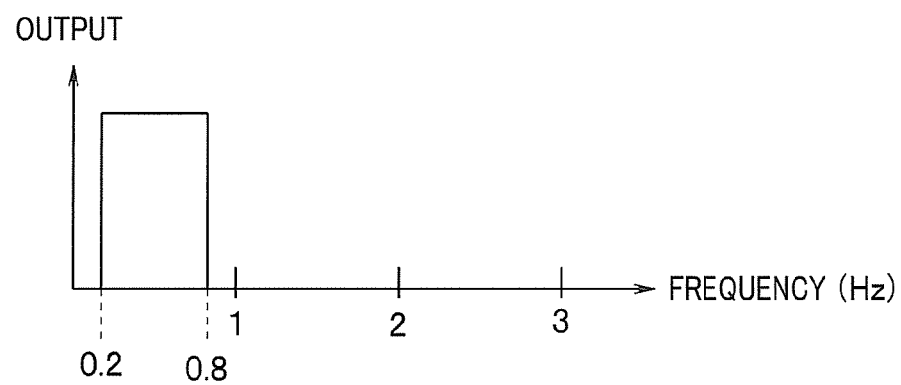
FIG. 5 is a graph showing filter characteristics of a band-pass filter 41a, according to the present embodiment.

FIG. 5 is a graph showing filter characteristics of the band-pass filter 41a. In FIG. 5, the horizontal axis indicates frequency while the vertical axis indicates output as an output signal. Note that filter characteristics of the band-pass filters 41b and 41c are same as the filter characteristics of the band-pass filter 41a.

Generally, frequency of arm swings at the time of walking is about 1 Hz, and frequency of arm swings at the time of running is about not less than twice the frequency at the time of walking. In contrast, in the case of an action other than walking, such as gymnastics or eating, the individual axis directions of the acceleration sensor 11 change relatively slowly and greatly.

As shown in FIG. 5, the band-pass filters 41a to 41c are filters configured to pass frequency components from 0.2 Hz to 0.8 Hz. With the use of the band-pass filters 41a to 41c having the filter characteristics shown in FIG. 5, only when the individual axis directions of the acceleration sensor 11 change slowly and greatly with respect to the gravity direction, signals corresponding to the changes are output from the band-pass filters 41a to 41c. As described above, the gravity detection unit 15 with the band-pass filters 41a to 41c configured to pass components within a predetermined frequency range constitutes a direction change detection unit configured to detect changes in the individual axis directions of the acceleration sensor 11 with respect to the gravity direction. More specifically, the gravity detection unit 15 as the direction change detection unit detects a change in an angle which a gravitational acceleration direction forms with each axis direction of the acceleration sensor 11. That is, since the acceleration sensor 11 is constantly affected by gravity, values from the acceleration sensor 11 change separately with changes in angles between the gravitational acceleration direction and the individual axis directions.

Figures 6A, 6B:
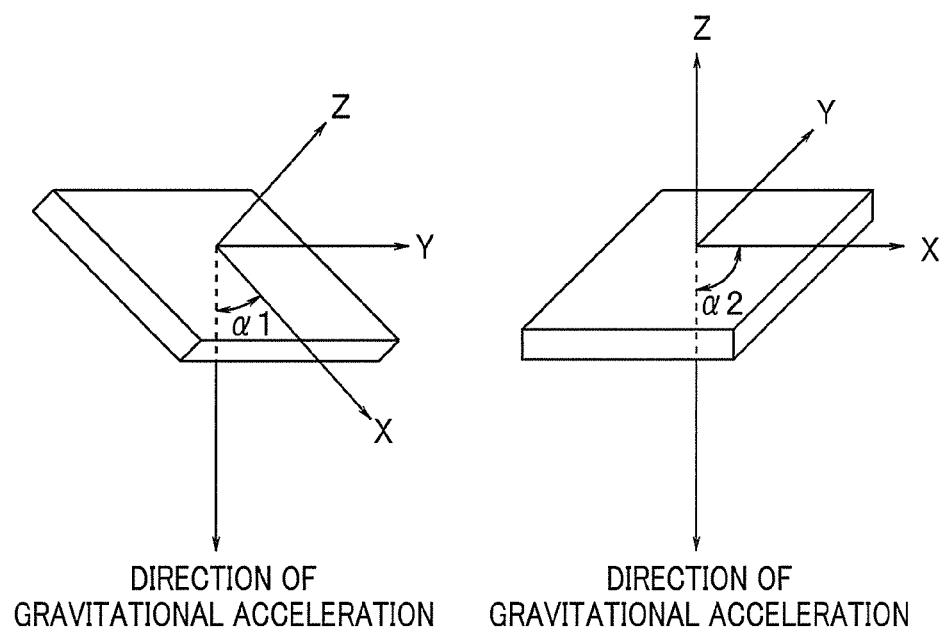
FIGS. 6A and 6B are views for explaining a change in an angle which a direction of gravitational acceleration forms with an X-axis direction of an acceleration sensor 11, according to the present embodiment.

FIGS. 6A and 6B are views for explaining a change in an angle which the direction of gravitational acceleration and the X-axis direction of acceleration sensor 11.

When the acceleration sensor 11 has the orientation shown in FIG. 6A, an angle which the direction of gravitational acceleration forms with the X-axis direction of the acceleration sensor 11 is α1. If the orientation of the acceleration sensor 11 changes to the orientation shown in FIG. 6B due to a user's action, the angle which the direction of gravitational acceleration forms with the X-axis direction of the acceleration sensor 11 becomes α2. When the angle which the direction of gravitational acceleration forms with the X-axis direction of the acceleration sensor 11 changes from α1 to α2, a value as an X-axis output from the acceleration sensor 11 also changes. The gravity detection unit 15 causes the band-pass filter 41a to pass a component as a change (motion) in the angle which the gravitational acceleration direction forms with the X-axis direction of the acceleration sensor 11 and detects the motion. The gravity detection unit 15 also performs detection for the Y-axis direction and the Z-axis direction of the acceleration sensor 11 to detect changes in the angles which the gravitational acceleration direction forms with the individual axis directions of the acceleration sensor 11.

The outputs from the band-pass filters 41a to 41c are input to the absolute value circuits 42a to 42c, respectively. The absolute value circuits 42a to 42c calculate absolute values of the outputs from the band-pass filters 41a to 41c and output the absolute values to the summation circuit 43.

The summation circuit 43 sums up the outputs from the absolute value circuits 42a to 42c and outputs a sum to the low-pass filter 44. The low-pass filter 44 averages outputs from the summation circuit 43 and produces a determination signal. The determination signal is output to the action determination and estimation unit 31 of the control unit 16.

As shown in FIG. 3, the control unit 16 includes the action determination and estimation unit 31, a counter unit 32, a memory 33, an event information recording transmission unit 34, and a wireless transmission unit 35. The control unit 16 includes a central processing unit (CPU), a ROM, and a RAM and implements a part of functions of the action determination and estimation unit 31 and the event information recording transmission unit 34 by software.

The action determination and estimation unit 31 determines whether a current action is walking or running (hereinafter referred to as walking without distinguishing between walking and running if not otherwise specified) or other than walking, by comparing the determination signal from the gravity detection unit 15 with a predetermined threshold. The action determination and estimation unit 31 is connected to a clock unit 53 to be described later so as to be capable of receiving a piece of time information.

FIGS. 7A and 7B are graphs for explaining examples of outputs from the acceleration sensor 11 and the gravity detection unit 15 during walking. FIGS. 8A and 8B are graphs for explaining examples of outputs from the acceleration sensor 11 and the gravity detection unit 15 during gymnastics. Note that FIG. 7A shows outputs from the acceleration sensor 11 during walking while FIG. 7B shows an output from the gravity detection unit 15 during walking. Similarly, FIG. 8A shows outputs from the acceleration sensor 11 during gymnastics while FIG. 8B shows an output from the gravity detection unit 15 during gymnastics.

In FIGS. 7A and 7B, outputs during walking are shown around between 120 to 460 seconds. In FIGS. 8A and 8B, outputs during gymnastics are shown around between 100 to 230 seconds.

As shown in FIG. 7B, the output from the gravity detection unit 15, or more specifically, an output from the low-pass filter 44 is small and negligible during walking. In contrast, as shown in FIG. 8B, the output from the gravity detection unit 15, or more specifically, an output from the low-pass filter 44 is large during an action other than walking which is gymnastics here. The action determination and estimation unit 31 determines on the basis of the output from the gravity detection unit 15 whether a current action is walking or is other than walking.

The action determination and estimation unit 31 adds a count value of the step counter 13 to a counter 32a for walking of the counter unit 32 if a current action is determined to be walking on the basis of an output from the gravity detection unit 15.

More specifically, the action determination and estimation unit 31 determines, on the basis of an output from the gravity detection unit 15 in a cycle of predetermined length (e.g., 5 seconds), whether a current action is walking or an action other than walking and, if the current action is determined to be walking, adds the count value of the step counter 13 during an immediately preceding cycle of the predetermined length (e.g., 5 seconds) to a count value of the counter 32a for walking.

Note that the count value is set to 0 (zero) in the counter 32a for walking to set the number of steps to 0 (zero) when the reset button (not shown) or the like is pressed, and an operation signal OP as a reset signal is produced.

The count value of the counter 32a for walking is recorded in the memory 33 every fixed time period.

As described above, the counter unit 32 includes the counter 32a for walking, and the counter 32a for walking counts up the number of steps when a user is walking.

If the action determination and estimation unit 31 determines that a current action is other than walking, by comparing a determination signal from the gravity detection unit 15 with the predetermined threshold, the action determination and estimation unit 31 estimates the type of the action other than walking on the basis of an acceleration intensity from the acceleration energy detection unit 14.

Figure 9A:
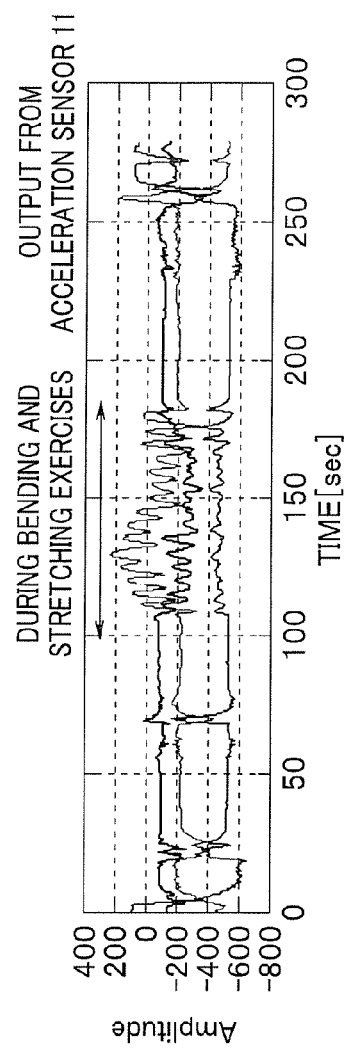
FIGS. 9A, 9B, and 9C are graphs for explaining examples of outputs from the acceleration sensor 11, the gravity detection unit 15, and an acceleration energy detection unit 14 during bending and stretching exercises, according to the present embodiment.
Figure 9B:
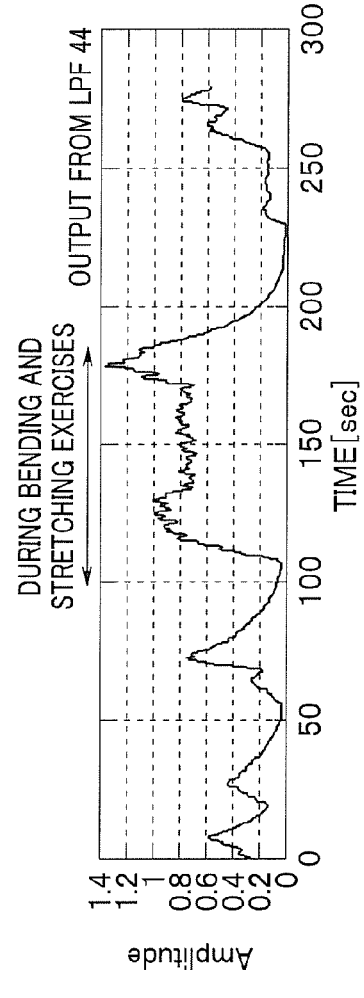
Figure 9C:
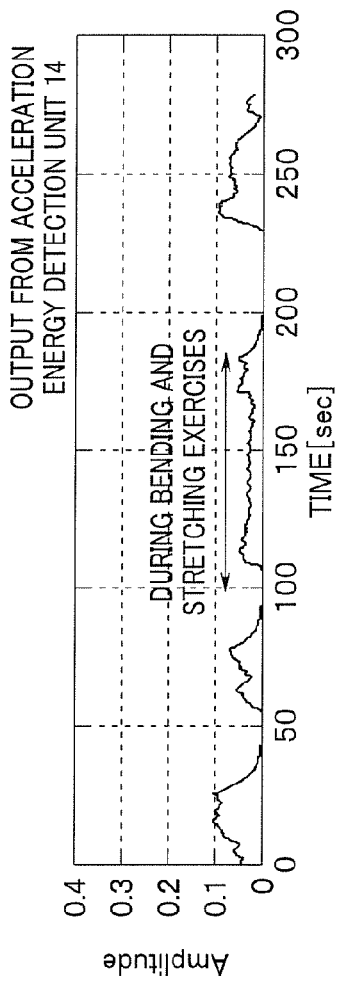

FIGS. 9A, 9B, and 9C are graphs for explaining examples of outputs from the acceleration sensor 11, the gravity detection unit 15, and the acceleration energy detection unit 14 during bending and stretching exercises. FIGS. 10A to 10C are graphs for explaining examples of outputs from the acceleration sensor 11, the gravity detection unit 15, and the acceleration energy detection unit 14 during practice swings with a tennis racket. Note that FIG. 9A shows outputs from the acceleration sensor 11 during bending and stretching exercises, FIG. 9B shows an output from the gravity detection unit 15 during bending and stretching exercises, and that FIG. 9C shows an output from the acceleration energy detection unit 14 during bending and stretching exercises. Similarly, FIG. 10A shows outputs from the acceleration sensor 11 during practice swings with a tennis racket, FIG. 10B shows an output from the gravity detection unit 15 during practice swings with a tennis racket, and that FIG. 10C shows an output from the acceleration energy detection unit 14 during practice swings with a tennis racket.

In FIGS. 9A, 9B, and 9C, outputs during bending and stretching exercises are shown around between 100 to 180 seconds. In FIGS. 10A, 10B, and 10C, outputs during practice swings with a tennis racket are shown around between 100 to 260 seconds.

The action determination and estimation unit 31 determines from the outputs from the gravity detection unit 15 shown in FIGS. 9B and 10B that actions in question are actions other than walking and estimates the actions other than walking (bending and stretching exercises and practice swings with a tennis racket) from the outputs from the acceleration energy detection unit 14 shown in FIGS. 9C and 10C.

Note that an action other than bending and stretching exercises and practice swings with a tennis racket can be similarly estimated from an output from the acceleration energy detection unit 14. The action determination and estimation unit 31 may estimate an action in question to be an action at any one of exercise intensity levels, e.g., low, medium, and high by comparing an output from the acceleration energy detection unit 14 with predetermined thresholds and obtain calorie consumption (energy consumption) corresponding to the exercise intensity level.

The action determination and estimation unit 31 stores such an estimation result in the memory 33. As described above, the memory 33 constitutes a storage unit configured to store an estimation result obtained through estimation by the action determination and estimation unit 31.

The wireless transmission unit 35 is a circuit for wireless communication, such as BlueTooth (registered trademark) or WiFi. In response to a transmission instruction from the action determination and estimation unit 31, a piece of estimation result information stored in the memory 33 is transmitted to the smartphone 2. Note that the wireless transmission unit 35 also transmits a piece of action information and a piece of time information which are recorded to the smartphone 2, in response to an instruction from the event information recording transmission unit 34, as will be described later.

As described above, if a current action is determined to be other than walking, the action determination and estimation unit 31 can more accurately estimate the type of the action other than walking by performing action estimation on the basis of an acceleration intensity from the acceleration energy detection unit 14.

The event information recording transmission unit 34 will now be described. The event information recording transmission unit 34 includes the arm motion determination unit 51, a recording unit 52, the clock unit 53, and a timer 54.

The clock unit 53 is a circuit configured to produce a piece of time information, and the arm motion determination unit 51 can refer to the piece of time information in the clock unit 53. The piece of time information includes information on a date and a time.

The timer 54 is a circuit configured to measure time to see whether a predetermined time period has elapsed. The timer 54 starts counting down in response to a timer-on instruction from the arm motion determination unit 51 and, when the predetermined time period has elapsed, times out. The predetermined time period is, for example, 2 seconds. The timer 54 continues outputting a signal indicating whether the timer 54 has timed out during a period from when the timer 54 is turned on to when the timer 54 times out. Thus, the arm motion determination unit 51 can determine whether the timer 54 has timed out by referring to an output status of the timer 54.

To the arm motion determination unit 51, a signal from the switch 3a of the operation button 3 and individual outputs from the acceleration sensor 11 are input. The arm motion determination unit 51 determines on the basis of individual outputs from the acceleration sensor 11 whether there is a predetermined motion of the arm L, when the operation button 3 is pressed. That is, the arm motion determination unit 51 constitutes a determination unit configured to determine on the basis of outputs from the acceleration sensor 11 whether there is a predetermined motion within the predetermined time period, when it is detected that the operation button 3 is operated and that there is a predetermined signal from the operation button 3.

There are a plurality of kinds of predetermined motions, and a piece of data for determining each motion is registered in advance as a piece of reference data in a storage unit 51a which is a rewritable, nonvolatile memory of the arm motion determination unit 51.

The arm motion determination unit 51 supplies information on a determined predetermined motion (hereinafter referred to as a piece of predetermined motion information) to the recording unit 52 if it is determined that there is the predetermined motion. Upon receipt of the piece of predetermined motion information, the recording unit 52 reads out the piece of time information from the clock unit 53 and outputs a command signal for causing a piece of event information corresponding to the piece of predetermined motion information and the read-out piece of time information to be recorded in the memory 33. The piece of predetermined motion information supplied from the arm motion determination unit 51 to the recording unit 52 may be a name (e.g., eating, medicine taking, or excretion) of a predetermined motion, a piece of code information (e.g., a number) determined in advance for each motion, or the like.

FIG. 11 is a graph for explaining an example of individual outputs from the acceleration sensor 11 when there is a predetermined motion of the arm L. FIG. 11 shows individual outputs from the acceleration sensor 11 when a wrist of the hand H is rotationally moved around an axis of the arm L twice quickly as a predetermined motion M1 of the arm, as indicated by chain double-dashed lines RM in FIG. 1.

When the hand H is rotationally moved twice quickly within a predetermined time period (e.g., within 2 seconds) after the operation button 3 is pressed, a Y-axis output does not change greatly while an X-axis output and a Z-axis output change greatly around 50 msec, as shown in FIG. 11.

FIG. 12 is a graph for explaining another example of individual outputs from the acceleration sensor 11 when there is a predetermined motion of the arm. FIG. 12 shows individual outputs from the acceleration sensor 11 when the hand H is caused to perform a movement that raps twice quickly (tapping movement) as a predetermined motion M2 of the arm.

When the hand H is caused to perform a movement to rap only twice quickly within a predetermined time period (e.g., within 2 seconds) after the operation button 3 is pressed, individual outputs as an X-axis output, a Y-axis output, and a Z-axis output change greatly around 50 msec, as shown in FIG. 12.

Pieces of waveform pattern information of the X-axis output, the Y-axis output, and the Z-axis output for each of the two predetermined motions M1 and M2 shown in FIGS. 11 and 12 are registered in advance as reference patterns for pattern recognition in the storage unit 51a within the arm motion determination unit 51. The arm motion determination unit 51 determines whether the arm L has made a predetermined motion by determining through pattern matching processing whether respective waveform patterns of an X-axis output, a Y-axis output, and a Z-axis output from the acceleration sensor 11 coincide with individual waveform patterns registered. The arm motion determination unit 51 outputs a piece of predetermined motion information indicating a determined predetermined motion to the recording unit 52.

By determining through waveform pattern matching processing whether respective waveform patterns of an X-axis output, a Y-axis output, and a Z-axis output from the acceleration sensor 11 coincide with the waveform patterns shown in FIGS. 11 and 12, a determination as to whether there is a predetermined motion M1 or M2 of the arm L can be made.

Two examples of a predetermined motion have been illustrated here. A piece of data for an arm motion other than the above-described two motions M1 and M2 as a predetermined motion of an arm is also recorded in advance as a piece of reference data in the storage unit 51a.

Upon receipt of a piece of predetermined motion information from the arm motion determination unit 51, the recording unit 52 records a piece of event information corresponding to the piece of predetermined motion information and a piece of time information at the time of reception of the piece of predetermined motion information in a predetermined storage area of the memory 33, a predetermined table TBL here. The recording unit 52 produces a piece of time information on the basis of the piece of time information from the clock unit 53.

Thus, when a user makes an arm motion corresponding to an action, such as eating, which the user performs or has performed, the user can regard the action as one event and record a piece of event information for the event and a piece of time information at the time of the arm motion in the activity tracker 1.

For example, assume that a user wants to record times of two actions, "eating" and "medicine taking." When the user makes the predetermined motion M1 within a predetermined time period since a press of the operation button 3 before or after eating, a piece of event information for "eating" and a piece of time information of the predetermined motion M1 are associated with each other and are recorded in the table TBL of the memory 33 in the activity tracker 1. When the user is to take a medicine after meal, the user makes the predetermined motion M2 within a predetermined time period since a press of the operation button 3 before or after the medicine taking. In the case, a piece of event information for "medicine taking" and a piece of time information of the predetermined motion M2 are associated with each other and are recorded in the table TBL of the memory 33 in the activity tracker 1.

(Workings)
(Action Determination and Estimation)

When the power to the activity tracker 1 is on, the activity tracker 1 is generally measuring the number of steps and executing estimation processing for the actions shown in FIGS. 7A to 10C.

When a user acts with the activity tracker 1 worn on an arm unit, output values for the individual axes detected by the acceleration sensor 11 are input to the acceleration detection unit 12 and the gravity detection unit 15. The output values for the individual axes detected by the acceleration sensor 11 are input to the acceleration detection unit 12, and an acceleration signal is detected. The acceleration signal detected by the acceleration detection unit 12 is input to the acceleration energy detection unit 14, and an acceleration intensity is detected. The acceleration intensity is input to the action determination and estimation unit 31.

The output values for the individual axes detected by the acceleration sensor 11 are input to the band-pass filters 41a to 41c of the gravity detection unit 15. Frequency components at the time of walking are removed from the output values for the individual axes by the band-pass filters 41a to 41c that pass frequency components from 0.2 Hz to 0.8 Hz. Only when the individual axis directions of the acceleration sensor 11 have changed slowly and greatly with respect to the gravity direction, signals corresponding to the changes are output.

Absolute values of outputs from the band-pass filters 41a to 41c are calculated by the absolute value circuits 42a to 42c, respectively. Outputs from the absolute value circuits 42a to 42c are summed up in the summation circuit 43. Outputs from the summation circuit 43 are averaged in the low-pass filter 44. A result is output as a determination signal to the action determination and estimation unit 31.

When the user is performing an action other than walking, the individual axis directions of the acceleration sensor 11 change slowly with respect to the gravity direction. Only when the individual axis directions of the acceleration sensor 11 change slowly and greatly with respect to the gravity direction, the band-pass filters 41a to 41c output signals corresponding to the changes. For the reason, the action determination and estimation unit 31 can determine whether a current action is walking or other than walking, by comparing a determination signal produced from outputs from the band-pass filters 41a to 41c with a predetermined threshold.

If the action determination and estimation unit 31 determines that a current action is other than walking, the action determination and estimation unit 31 estimates the type of the action other than walking on the basis of an acceleration intensity from the acceleration energy detection unit 14.

The action determination and estimation unit 31 stores the value of the walking counter 32a, i.e., the number of steps in the memory 33. The action determination and estimation unit 31 also stores a result of estimating an action of a user in the memory 33. When the action determination and estimation unit 31 stores the result of estimating the action of the user in the memory 33, the action determination and estimation unit 31 stores the result together with a current time. The activity tracker 1 can acquire a result of estimating actions of a user for one day by storing a result of estimating an action of the user and a piece of time information indicating a current time from the clock unit 53 in association with each other.

As described above, the activity tracker 1 can acquire an action pattern of a user for one day, such as how many hours the user has performed exercises including gymnastics, or a lifestyle of the user, by acquiring a result of estimating actions of the user for one day. A doctor can give best advice on improvement in living environment and lifestyle to a patient afflicted with lifestyle-related diseases by, for example, attaching the activity tracker 1 to an arm unit of the patient and acquiring an action pattern of the patient for one day.

(Event Recording)

When a user presses the operation button 3, the activity tracker 1 executes an event information recording transmission process.

Figure 13:
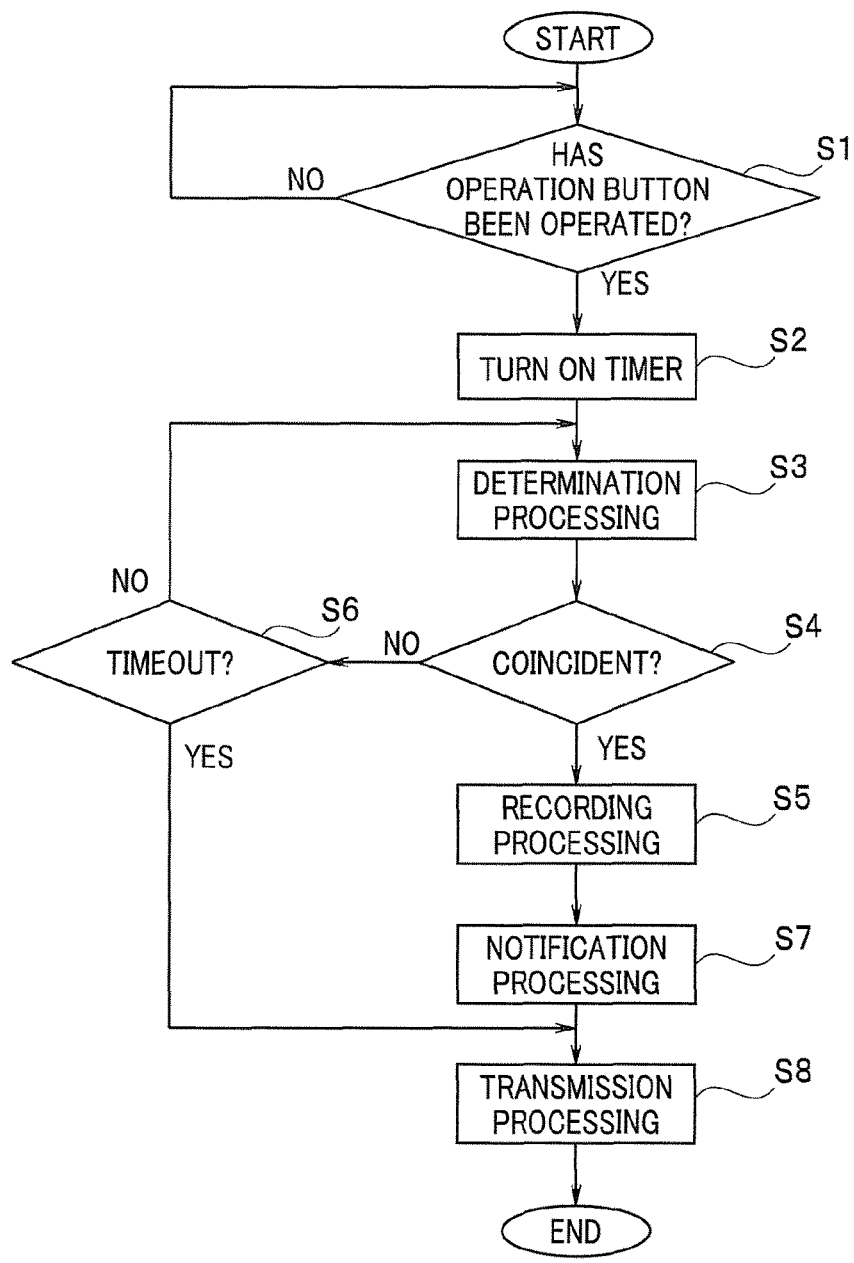
FIG. 13 is a flowchart showing an example of a flow of a time recording transmission process, according to the present embodiment.

The arm motion determination unit 51 executes the process in FIG. 13 upon sensing that the operation button 3 is pressed.

FIG. 13 is a flowchart showing an example of a flow of the event information recording transmission process.

The arm motion determination unit 51 first determines whether the operation button 3 is pressed (S1). The processing in S1 constitutes a detection processing unit configured to detect presence or absence of a predetermined signal that is not an output signal from the acceleration sensor 11. The detection processing in S1 detects a signal from the switch 3a as the predetermined signal. If the arm motion determination unit 51 does not sense that the operation button 3 is pressed (S1: NO), the arm motion determination unit 51 performs no processing.

If the arm motion determination unit 51 senses that the operation button 3 is pressed (S1: YES), the arm motion determination unit 51 turns on the timer 54 (S2). When the timer 54 is turned on, the timer 54 measures time for a predetermined time period (e.g., 2 seconds). The arm motion determination unit 51 turns on the timer 54 and then executes determination processing (S3).

The determination processing monitors three outputs, an X-axis output, a Y-axis output, and a Z-axis output from the acceleration sensor 11 to determine whether input waveforms of the three outputs coincide with any one of a plurality of waveform patterns registered in advance in the storage unit 51a. As described above, the determination about coincidence is performed through pattern matching processing. The pattern matching processing determines through comparison whether three pieces of waveform data of the X-axis output, the Y-axis output, and the Z-axis output coincide with three pieces of waveform data of an X-axis output, a Y-axis output, and a Z-axis output of each waveform pattern registered in advance.

If a result of the determination processing shows that the three pieces of waveform data of the X-axis output, the Y-axis output, and the Z-axis output from the acceleration sensor 11 coincide with three pieces of waveform data of an X-axis output, a Y-axis output, and a Z-axis output of any one of the waveform patterns registered in advance (S4: YES), the arm motion determination unit 51 outputs a piece of predetermined motion information corresponding to the three coincident pieces of waveform data to the recording unit 52, as described above.

As described above, the arm motion determination unit 51 determines a movement of an arm within a predetermined time period since operation of the operation button 3, which allows accurate determination of presence or absence of a predetermined arm movement. Additionally, the determination processing is executed only within the predetermined time period, and power consumed by the activity tracker 1 can be reduced.

The recording unit 52 that has received the piece of predetermined motion information performs recording processing (S5).

The recording unit 52 associates a piece of event information as a piece of corresponding information corresponding to the received piece of predetermined motion information with a piece of time information and writes the pieces of information as one pair of pieces of information to the memory 33. The piece of corresponding information corresponding to the piece of predetermined motion information is a piece of event code information here and is recorded in the table TBL of the memory 33. That is, the processing in S5 constitutes a recording processing unit configured to record an event information code as a piece of corresponding information corresponding to a determined predetermined motion and a piece of time information in the memory 33.

Figure 14:
FIG. 14 is a chart showing an example of pieces of event information and pieces of time information recorded in a memory 33, according to the present embodiment.

FIG. 14 is a chart showing an example of pieces of event information and pieces of time information recorded in the memory 33. A piece of event information and a piece of time information are recorded in association with each other in the table TBL in the memory 33. As shown in FIG. 14, an event code of "1" indicating that "eating" was performed at 7:30 on Dec. 19, 2013 is recorded, and an event code of "2" indicating that "medicine taking" was performed at 8:10 on Dec. 19, 2013 is recorded.

If the result of the determination processing shows that the three pieces of waveform data of the X-axis output, the Y-axis output, and the Z-axis output from the acceleration sensor 11 do not coincide with three pieces of waveform data of an X-axis output, a Y-axis output, and a Z-axis output of any one of the waveform patterns registered in advance (S4: NO), the arm motion determination unit 51 determines from an output status of the timer 54 whether the timer 54 has timed out after a lapse of the predetermined time period (e.g., 2 seconds) since the turn-on of the timer 54 (S6). If the timer 54 has not timed out (S6: NO), the process shifts to S3 to execute the determination processing (S3). On the other hand, if the timer 54 has timed out (S6: YES), the process ends.

When the recording processing is executed (S5), the arm motion determination unit 51 executes notification processing (S7). The notification processing is a process of causing the lamp 4 to glow according to a determined event. The arm motion determination unit 51 controls light emission of the lamp 4 such that the lamp 4 glows once if an event code corresponding to the waveform pattern registered in advance that is determined to be coincident is "1." The arm motion determination unit 51 controls light emission of the lamp 4 such that the lamp 4 glows twice if the event code corresponding to the waveform pattern registered in advance that is determined to be coincident is "2." Thus, the processing in S7 constitutes an output unit configured to, if it is determined in S3 that there is a predetermined motion, produce a predetermined output to notify a user of the determination.

Note that although the lamp 4 is caused here to glow times corresponding to each event information code, the lamp 4 may be caused to glow once for any event information code.

Since the lamp 4 emits light after the user causes the arm L to make a predetermined motion within the predetermined time period after a press of the operation button 3, the user can know that the predetermined motion made of the arm is recognized by the activity tracker 1. If the lamp 4 does not emit light after the user causes the arm L to make the predetermined motion within the predetermined time period after a press of the operation button 3, the user knows that the predetermined motion made of the arm is not recognized by the activity tracker 1.

The arm motion determination unit 51 performs transmission processing (S8). The transmission processing is a process of wirelessly transmitting an event information code and a piece of time information recorded in the memory 33 from the wireless transmission unit 35. Thus, the processing in S8 constitutes a transmission processing unit configured to wirelessly transmit an event code as a piece of corresponding information corresponding to the determined predetermined motion and a piece of time information at the time of detecting that the operation button 3 is pressed and that there is a predetermined input, when it is determined in the processing in S3 that there is a predetermined motion of the arm. That is, the arm motion determination unit 51 transmits the piece of corresponding information and the piece of time information from the wireless transmission unit 35 immediately when it is determined in S3 that there is a predetermined motion.

Note that an event code and a piece of time information may not be transmitted immediately in the transmission processing except in an emergency or in the case of a specific motion. That is, the activity tracker 1 may not transmit an event code and a piece of time information right away except in an emergency or in the case of a specific motion but may transmit an event code and a piece of time information in real time in an emergency or in the case of a specific motion of an arm.

For example, a motion of an arm in an emergency is registered in advance. When a user presses the operation button 3 and makes a predetermined motion (a motion different from the above-described predetermined motions M1 and M2) corresponding to an emergency, such as a case where the user tumbles and needs help, an event information code of an event representing an emergency and a piece of time information are transmitted right away.

For a non-emergency event, such as "eating" or "medicine taking," the arm motion determination unit 51 monitors the piece of time information in the clock unit 53 and executes transmission processing that wirelessly transmits an event code and a piece of time information recorded in the table TBL of the memory 33 at a predetermined time, such as 12:00 midnight. That is, in the transmission processing, event codes and pieces of time information recorded in the memory 33 are transmitted all together from the wireless transmission unit 35 at the predetermined time.

Note that the arm motion determination unit 51 may wirelessly transmit a piece of action information recorded in the table TBL of the memory 33 every predetermined time period, such as 3 hours, on the basis of the piece of time information in the clock unit 53.

That is, the arm motion determination unit 51 may transmit pieces of corresponding information and pieces of time information recorded in the memory 33 from the wireless transmission unit 35 at a predetermined time or at predetermined time intervals. In the case, it is determined in S3 which one of a plurality of predetermined motions is present, on the basis of outputs from the acceleration sensor 11. The arm motion determination unit 51 transmits a piece of corresponding information and a piece of time information immediately if the determined motion is a motion corresponding to an emergency or the like and transmits a piece of corresponding information and a piece of time information at a predetermined time or at predetermined time intervals if the determined motion is a motion other than a motion in an emergency or the like.

As has been described above, according to the above-described embodiment, a wristband-type arm movement determination device can be provided which can accurately determine presence or absence of a predetermined arm movement and can reduce power consumption.

In particular, since it is determined whether there is a predetermined motion of the arm L within a predetermined time period after there is a predetermined operation which a user performs with purpose (a press of the operation button 3 here), the probability of erroneous determinations in the arm motion determination unit 51 is low.

People have conventionally taken notes to keep a record of their actions. In particular, to record actions, times of the actions also need to be recorded and jotted down, which requires troublesome work.

In some cases, periodic measuring and recordkeeping of a piece of measurement data of a person are necessary. For example, a diabetic needs to periodically gauge and record a blood sugar level. To record whether a measured blood sugar level is a value before meal or a value after meal, the diabetic needs to carry a pocket notebook for data recording to record the data.

However, by registering in advance motions of an arm corresponding to actions, medicine taking before meal and medicine taking after meal, using the activity tracker 1 according to the embodiment, a user can label a piece of measured data, such as a blood sugar level, as before meal or after meal by means of the activity tracker 1 or the smartphone 2. That is, if the activity tracker 1 according to the embodiment is used, a before-eating state and an after-eating state are automatically recorded and transmitted as pieces of event information together with pieces of time information of the states, and the user can view and confirm a record of events or actions with the smartphone 2.

The above-described example is provided with only one operation button 3 and has the advantage that the activity tracker 1 is not large.

Note that a sensor may be used instead of the operation button 3. As indicated by dotted lines in FIG. 3, a sensor 3A is provided instead of the operation button 3, and the sensor 3A is connected to a detection unit 3Aa. The detection unit 3Aa determines whether an output signal from the sensor 3A has exceeded a predetermined threshold and, if the output signal exceeds the predetermined threshold, outputs the detected signal to the arm motion determination unit 51. That is, the detection processing in S1 detects an output signal from the sensor configured to detect a physical quantity as a predetermined signal.

In the case, the sensor 3A is a temperature sensor, a carbon dioxide sensor, or the like. When a user touches a temperature sensor, the detection unit 3Aa detects a change in a detected temperature from the temperature sensor, and the detected signal is output to the arm motion determination unit 51.

As notification means, a predetermined sound or voice may be output from the speaker 5, instead of using light from the lamp 4. Alternatively, vibration may be used as notification means. For example, as indicated by a dotted line in FIG. 3, the activity tracker 1 may have a built-in vibrator 7 as notification means, and a user may be informed of a determination through vibration.

Alternatively, as indicated by a dotted line in FIG. 3, a display unit 17 like a liquid crystal display unit may be provided at the activity tracker 1, and a display indicating a piece of information, such as the number of steps, and that a motion of an arm is determined may be produced on the display unit 17. When a motion of an arm is determined, for example, the characters "determination" or characters indicating details of an action, such as the characters "eating" or "medicine taking," may be displayed.

Since the above-described activity tracker 1 is of a wristband type, the activity tracker 1 with the configuration shown in FIG. 3 may be incorporated in a wristwatch, and the wristwatch may be caused to have a function of an arm movement determination device as a function of the wristwatch.

While certain embodiments have been described, these embodiments have been presented by way of example only, and are not intended to limit the scope of the inventions. Indeed, the novel devices described herein may be embodied in a variety of other forms; furthermore, various omissions, substitutions and changes in the form of the devices described herein may be made without departing from the spirit of the inventions. The accompanying claims and their equivalents are intended to cover such forms or modifications as would fall within the scope and spirit of the inventions.

What is claimed is:

1. A wristband-type activity tracker wearable on an arm of a user comprising:
   an acceleration sensor capable of detecting accelerations in directions of two or more axes orthogonal to each other;
   an operation button configured to output a predetermined signal when operated by the user;
   a wireless transmission circuit;
   a control unit including a central processing unit; and
   a first memory in which data for determining a plurality of predetermined motions is registered,
   wherein the control unit executes, by the central processing unit, processes of:
   determining, from an acceleration signal for the directions of the two or more axes which is detected on the basis of an output from the acceleration sensor and a gravitational acceleration signal, whether an action of the user wearing the wristband-type activity tracker is walking or other than walking, and recording in a second memory, a piece of information on the determined action of the user and a piece of time information at a time when the action of the user is determined;
   detecting presence or absence of the predetermined signal;
   (i) determining on the basis of the data registered in the first memory and an output from the acceleration sensor whether there is any one of the plurality of predetermined motions within a predetermined time period, when it is detected that there is the predetermined signal, and not determining whether there is any one of the plurality of predetermined motions, when it is not detected that there is the predetermined signal;
   (ii) performing a predetermined output for notification according to the determined motion to the user when it is determined that there is one of the plurality of predetermined motions;
   (iii) wirelessly transmitting a piece of corresponding information corresponding to the determined motion and the piece of time information immediately from the wireless transmission circuit, if the determined motion is a first motion, and wirelessly transmitting the piece of corresponding information and the time information from the wireless transmission circuit at predetermined time intervals or at a predetermined time, if the determined motion is other than the first motion; and
   (iv) recording the piece of corresponding information and the piece of time information in the second memory when it is determined that there is one of the plurality of predetermined motions.

2. The wristband-type activity tracker according to claim 1, wherein
   the control unit executes, by the central processing unit, the process of determining whether there is any one of the plurality of predetermined motions by comparing a waveform pattern of the acceleration sensor, which is registered in advance and indicates the plurality of predetermined motions, with a waveform pattern of an output from the acceleration sensor to see whether the waveform patterns coincide with each other.

3. The wristband-type activity tracker according to claim 2, wherein
   if the control unit determines that the action of the user is an action other than walking, the control unit executes, by the central processing unit, a process of estimating a type of the action other than walking on the basis of an acceleration energy intensity detected from the acceleration signal.

4. The wristband-type activity tracker according to claim 1, wherein
   the operation button has a switch, and
   the control unit executes, by the central processing unit, a process of detecting a signal from the switch as the predetermined signal.

5. The wristband-type activity tracker according to claim 1, wherein the operation button has a sensor configured to detect a physical quantity, and the control unit executes, by the central processing unit, a process of detecting an output signal from the sensor as the predetermined signal.

6. The wristband-type activity tracker according to claim 5, wherein the sensor is a temperature sensor or a carbon dioxide sensor.

* * * * *